(12) United States Patent
Long

(10) Patent No.: US 6,296,149 B1
(45) Date of Patent: Oct. 2, 2001

(54) MONOMER DELIVERY DEVICE FOR BONE CEMENT DELIVERY SYSTEM

(75) Inventor: Jack F. Long, Warsaw, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/293,396

(22) Filed: Apr. 16, 1999

(51) Int. Cl.[7] .................................................. B67D 5/00
(52) U.S. Cl. ............................................................ 222/82
(58) Field of Search ........................................ 222/80, 82

(56) References Cited

U.S. PATENT DOCUMENTS

| Re. 35,276 | 6/1996 | Chan . |
| 4,787,751 | 11/1988 | Bakels . |
| 4,973,168 | 11/1990 | Chan . |
| 5,100,241 | 3/1992 | Chan . |
| 5,145,250 | 9/1992 | Planck et al. . |
| 5,152,432 | 10/1992 | De Laforcade . |
| 5,193,907 | 3/1993 | Faccioli et al. . |
| 5,252,301 | 10/1993 | Nilson et al. . |
| 5,328,262 | 7/1994 | Lidgren et al. . |
| 5,344,232 | 9/1994 | Nelson et al. . |
| 5,348,391 | 9/1994 | Murray . |
| 5,368,386 | 11/1994 | Murray . |
| 5,395,167 | 3/1995 | Murray . |
| 5,415,474 | 5/1995 | Nelson et al. . |
| 5,435,645 | * 7/1995 | Faccioli et al. ...................... 366/130 |
| 5,443,182 | 8/1995 | Tanaka et al. . |
| 5,505,538 | 4/1996 | Earle . |
| 5,545,460 | 8/1996 | Tanaka et al. . |
| 5,551,778 | 9/1996 | Hauke et al. . |
| 5,558,136 | 9/1996 | Orrico . |
| 5,586,821 | 12/1996 | Bonitati et al. . |
| 5,588,745 | 12/1996 | Tanaka et al. . |
| 5,875,928 | * 3/1999 | Muller et al. ........................... 222/82 |
| 6,042,262 | * 3/2000 | Hajianpour ........................... 366/139 |

FOREIGN PATENT DOCUMENTS

| 29 21 565 | 12/1980 | (DE) . |
| 195 32 015 | 3/1997 | (DE) . |
| WO-9960140 | * 11/1999 | (WO) .............................. B01F/13/06 |

* cited by examiner

Primary Examiner—Joseph A. Kaufman
Assistant Examiner—David Deal
(74) Attorney, Agent, or Firm—Maginot, Addison & Moore

(57) ABSTRACT

A monomer delivery device for a bone cement delivery system having a sealed body that has and a chamber sized to receive an ampule of monomer, a collar attached to the body having a blade configured to sever the ampule and a spout attached to the collar to expel the monomer.

20 Claims, 7 Drawing Sheets

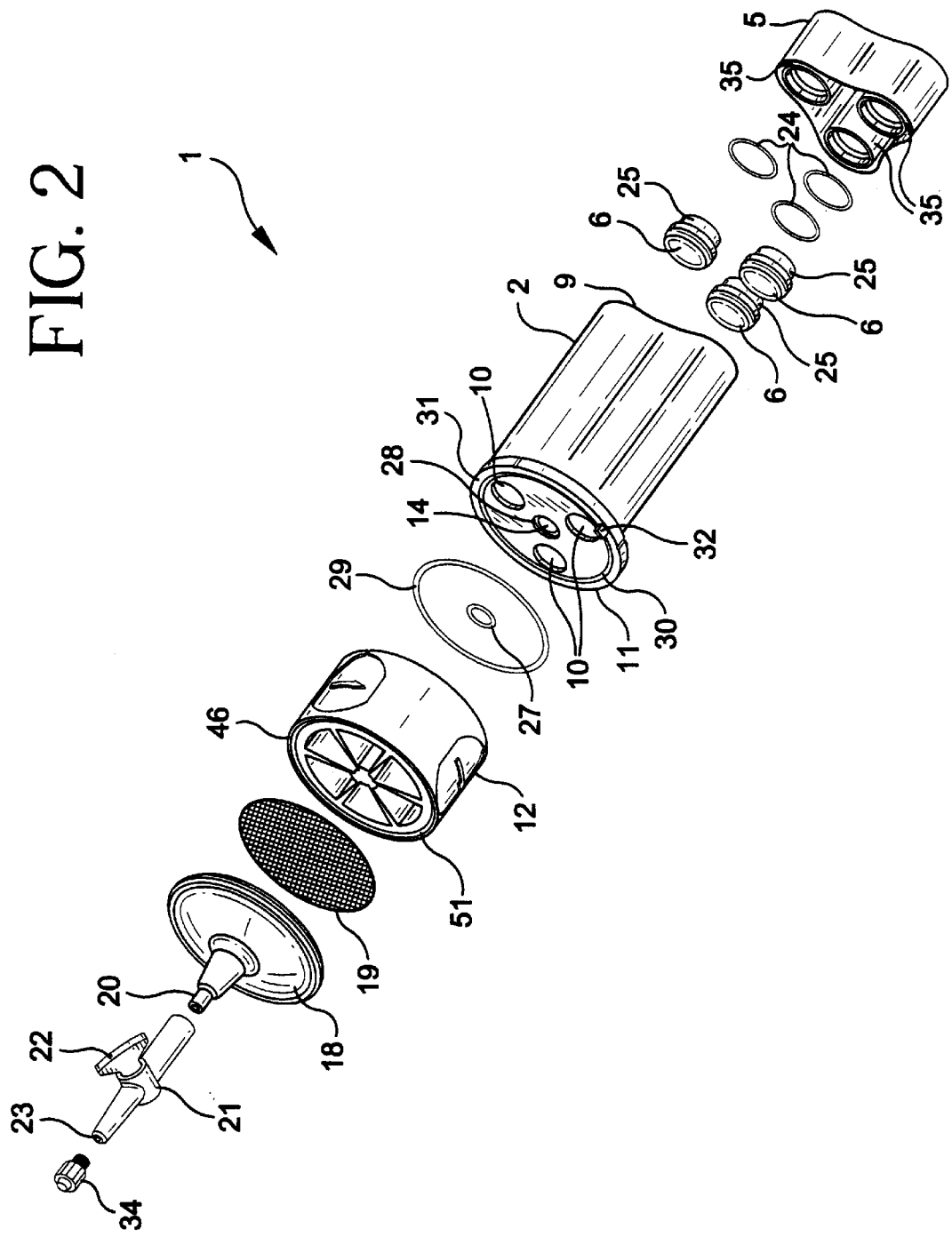

MONOMER DELIVERY DEVICE FOR BONE CEMENT DELIVERY SYSTEM

BACKGROUND AND SUMMARY OF THE INVENTION

The present invention relates to a monomer delivery device for a bone cement delivery system. More particularly, the present invention relates to a sealed monomer delivery device having a body that has a chamber sized to receive an ampule of monomer, a collar attached to the body having a blade configured to sever the ampule and a spout attached to the collar to expel the monomer.

It is well known that in many orthopedic surgical procedures it is necessary to employ a cement or grouting type agent, such as for attaching artificial joint implants, repairing or forming joints in bones, or other forms of orthopedic work. The type of cement generally used for these purposes are self-curing resins formed from the blending of a wide variety of liquid monomers or comonomers with powdered polymers or copolymers to form a viscous admixture to be used as the grouting agent. The admixture of the powder and liquid components develops a quick setting material and preparation of the cement usually occurs directly within the operating theater just prior to use. Monomer vapors, however, are noxious and toxic, and are generated during the depositing of the monomer and when mixing same with bone cement. And because making the bone cement mixture is conducted in the operating room environment, it is important not to allow any monomer or its vapors to escape the monomer delivery device except for deposit into the bone cement mixing system.

The present invention is primarily concerned with a device that will dispense monomer into a bone cement mixing apparatus without releasing monomer vapors into the environment. The present invention is designed to accept ampules of monomer, break said ampules in an encapsulated chamber, dispense monomer into a mixing device without allowing monomer vapors to escape, and to allow the user to either dispose or re-use the monomer dispensing device after the monomer has been expelled.

According to other features, characteristics, embodiments and alternatives of the present invention which will become apparent as the description thereof proceeds below, the present invention provides a monomer dispensing device comprising a body having a chamber containing liquid monomer, and a spout attached to the chamber for expelling monomer.

In one embodiment, the monomer dispensing device includes a body having a chamber sized to receive an ampule of monomer. A collar is attached to the body having a blade attached within the collar configured to sever the ampule. A spout is attached to the collar to expel the monomer.

In a further embodiment, the monomer dispensing device includes a body having a chamber sized to receive an ampule of monomer. The body also has a load end where the ampule is inserted into the chamber, and a cap end where an aperture is disposed therethrough. A cap on the ampule extends through the aperture. A post is positioned inside the chamber and abuts the ampule thereby securing same within the chamber. An end cap is attached to the load end of the body and has a post stop that limits the movement of the post. A rotating collar is pivotally attached to the cap end of the body and is positioned to receive the ampule cap. The rotating collar also has a plurality of blades configured to sever the ampule cap when the collar is rotated. A funnel is fitted on the rotating collar opposite the body such that as the monomer is released from the ampule it collects in the funnel. A screen is placed between the rotating collar and the funnel preventing particles from the severed ampule cap from traveling past the rotating collar and being deposited into the cement. A spout is attached to the funnel that expels the collected monomer.

BRIEF DESCRIPTION OF DRAWINGS

The present invention will be described hereafter with reference to the attached drawings which are given as non-limiting examples only, in which:

FIG. 2 is an exploded perspective view of the monomer dispensing device from FIG. 1, showing the o-rings between the different components of the device, and including a luer lock attached to the end of the valve;

DETAILED DESCRIPTION OF THE INVENTION

The present invention is directed to a monomer delivery device that is part of a bone cement dispensing system for use in a surgical operating room environment. The delivery device is configured to sever an ampule of monomer in a sealed structure and dispense the monomer into another container used for mixing bone cement. The monomer delivery device is sealed to prevent toxic fumes from escaping which could possibly endanger the operator. The following description is but one embodiment of the monomer dispensing device, and will be described with reference to FIGS. 1–14. While the described embodiment is considered by the inventor to be the best mode of carrying out the invention, it should be understood that the claims presented below are not limited to the particular details of the described embodiment. Numerous variations may be readily apparent to those of skill in the art which would provide for construction of a monomer delivery device which incorporate the principles of the present invention as claimed.

Figure 1:
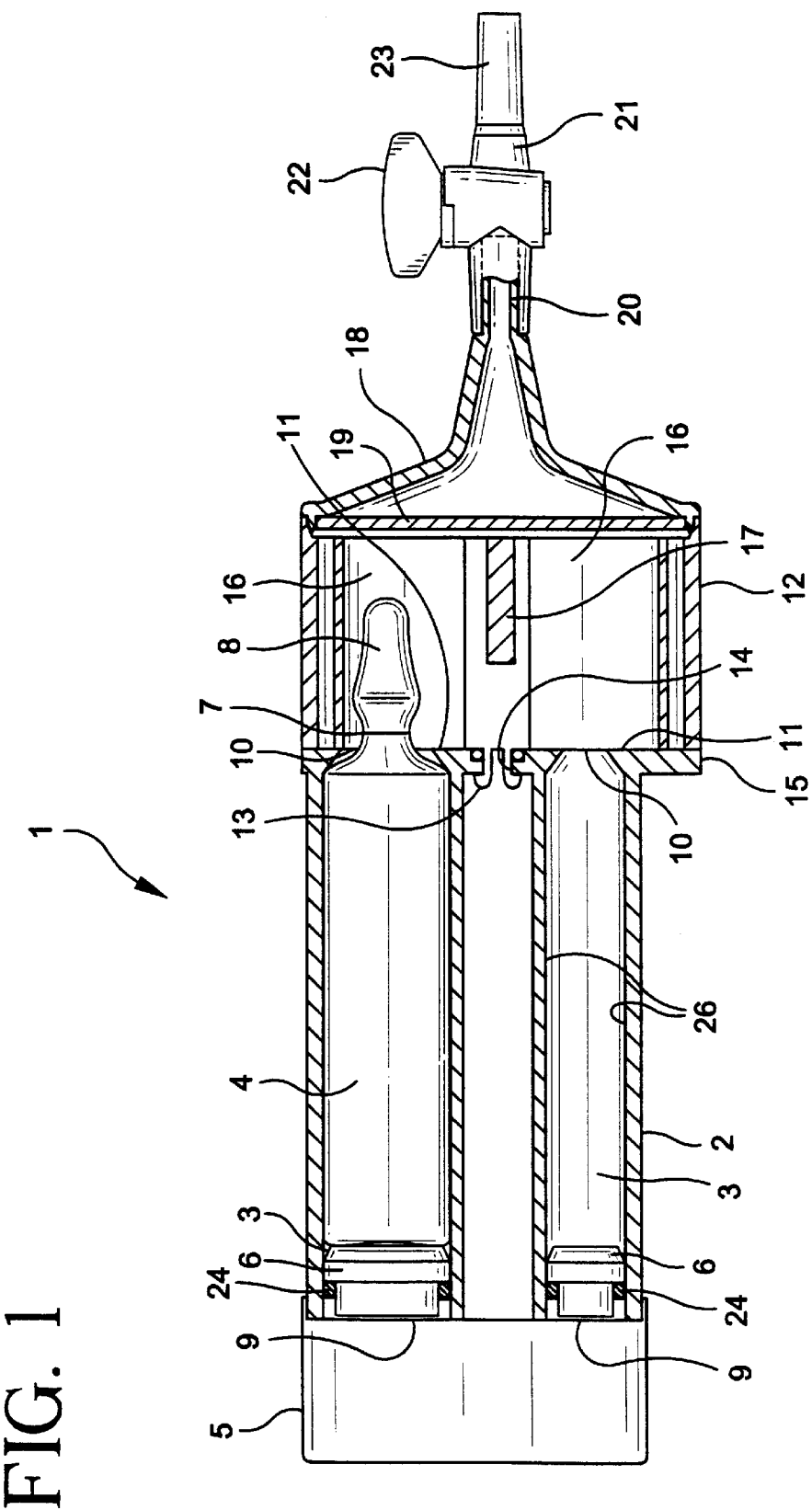
FIG. 1 is a sectional view of an assembled monomer delivery device embodying the invention showing a body, and an end cap, a rotating collar with blades, a funnel, a spout, and a nozzle.
Figure 4:
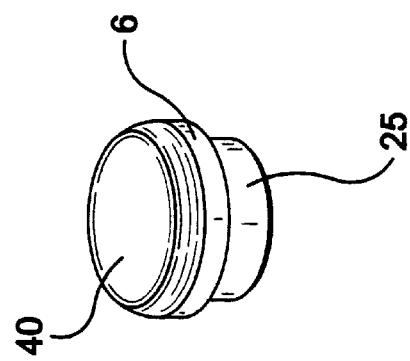
FIG. 4 is a perspective view of a post showing its plug and its top.

A monomer delivery device comprising a body 2 having an ampule chamber 3 sized to hold an ampule 4 of monomer for deposit to a quantity of bone cement, is shown in FIG. 1. It is understood that body 2 may comprise one ampule chamber 3 or a plurality of ampule chambers 3. End cap 5 attaches to body 2 after ampule 4 and a post 6 have been inserted into ampule chamber 3. Post 6 comprises a plug portion 25 and a top portion 40 (see FIG. 4) and is configured to abut ampule 4 so that ampule 4 is securely contained inside ampule chamber 3. It will be appreciated that the number of posts 6 that can be fitted into body 2 may correspond with the number of ampule chambers 3. It will also be appreciated that closures other than illustrated posts 6 may be used to securely hold ampule 4 in chamber 3.

One illustrated embodiment of ampule 4 may have a neck 7 on one end having an ampule cap 8 attached thereto. Monomer liquid is encapsulated inside ampule 4. Ampule 4 is placed inside ampule chamber 3 from load end 9 such that ampule cap 8 extends through an aperture 10 on cap end 11 of body 2. A collar 12 is rotatably attached to body 2 by a collar lock 13 to depend from the longitudinal axis of collar 12, and to extend through a collar lock aperture 14 also located on cap end 11. Collar 12 is movable about the longitudinal axis of body 2. A flange 15 is located on cap end 11 having substantially the same diameter as collar 12 and placed adjacent to collar 12 creating a seal.

Collar 12 illustratively has a plurality of broad flat bodies or blades having a length that extends along the longitudinal axis of collar 12 and are sufficiently rigid to sever ampule 4. In one embodiment shown in FIG. 1, the blade lengths alternate from a full depending blade 16 to a half depending blade 17. In this embodiment, half blade 17 depends about half the length of full blade 16 beginning opposite cap end 11 and extending the longitudinal axis of collar 12. (See also FIG. 7). As collar 12 rotates, half blade 17 contacts the tip of cap 8 on ampule 4 causing a shearing force on neck 7 resulting in the shear fracture of ampule at neck 7. Cap 8 is then completely broken and pushed away from ampule 4 by full blade 16. This allows monomer to flow from ampule 4 to collar 12 and eventually out of dispensing device 1. It is understood, however, that collar 12 may comprise any type, number, or configuration of blades so long as the blades are able to sever ampule 4. For example, collar 12 may comprise of one large blade, or a plurality of depending full blades.

Illustratively located between collar 12 and funnel 18 is a screen 19 to trap broken particles from ampule 4 in collar 12. The liquid monomer passes through screen 19 into funnel 18. At the end of funnel 18 opposite screen 19 is a spout 20. Liquid travels from funnel 18 out through spout 20 into a mixing device (not shown) to be combined with the bone cement. The monomer can either be deposited and combined with the bone cement directly from spout 20, or, in one illustrative embodiment, the monomer can be deposited into a sealable valve 21 that attaches to spout 20. Valve 21 includes a valve closure 22 that allows the monomer to flow out of a valve hole 23 at the discretion of the operator when closure 22 is disengaged, and prevents the monomer from flowing out of valve hole 23 when closure 22 is engaged.

An exploded perspective view of monomer dispensing device 1 is shown in FIG. 2. When device 1 is assembled, o-rings are placed between major components to keep the monomer and the monomer vapor encapsulated inside device 1 and only released through valve hole 23. A medium o-ring 24 is circumferentially fitted around plug 25 (see FIG. 4) of post 6 behind abutting inner wall 26 (see FIGS. 1, 4 and 6) of ampule chamber 3. As post 6 is inserted into ampule chamber 3, medium o-ring 24 creates a seal between post 6 and inner wall 26 preventing any vapors from escaping at that joint (see FIG. 1). Because ampules 4 can be of varied lengths, post 6 can travel linearly along inner chamber 3 to securely hold ampule 4.

A small o-ring 27 may be placed between collar latch 13 (see FIG. 1) and collar latch aperture 14. Small o-ring 27 may be circumferentially fitted around collar latch 13 and seated in an o-ring groove 28, which itself is circumferentially formed on latch aperture 14. This creates a seal between collar latch 13 and collar latch aperture 14.

A large o-ring 29 may be placed between collar 12 and body 2. Large o-ring 29 may be fitted circumferentially around body 2 in a groove 30 near flange 31. When collar 12 is attached to body 2, both small o-ring 27 and large o-ring 29 seal any gaps between collar 12 and body 2 so no monomer vapors or liquid can escape.

Figure 8:
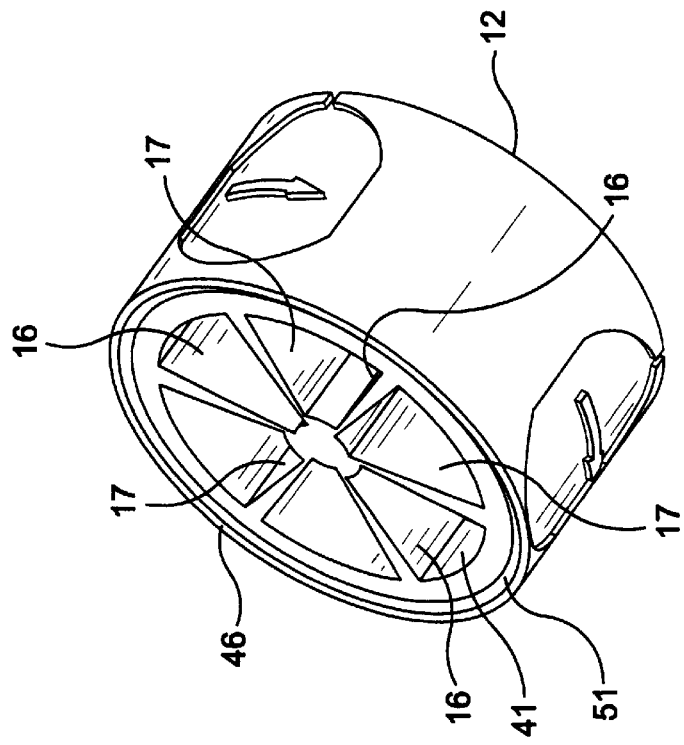
FIG. 8 is a rear perspective view of a portion of the monomer delivery device from FIG. 2, showing the rotating collar having the plurality of half blades and full blades, a collar lock depending from the convergence of the blades, and a tab groove formed inside the collar about the circumference of the bottom end.

A tab 32 is illustratively shown in FIG. 2, extending from flange 31 on cap end 11 of body 2. Tab 32 cooperates with a tab groove 33 (see FIG. 8) in collar 12 to limit collar 12 to a predefined, range of movement about a portion of the collar's circumference. As shown in FIG. 8, tab groove 33 is formed within a portion of the circumference of bottom end 42. Tab groove 33 is approximately one quarter the circumference of collar 12. When collar 12 is pivotally attached to body 2, tab 32 extends from flange 31, and is fitted into tab groove 33. This restricted movement allows only a limited number of blades to sever a particular ampule cap 8 and once tab 32 abuts the end of groove 33, the blades are positioned such that they are not inadvertently covering the severed ampule restricting the flow of monomer. It is understood, however, that collar 12 and the blades 16 and 17 may be configured to sever ampule 4 in a variety of ways; for example, the collar may rotate in a completely, 360 degree circumference about the longitudinal axis, or, the collar may be moved axially inward along the longitudinal axis.

A luer lock 34,(also shown in FIG. 2), is configured to attach to valve 21 and then mate with a luer on a mixing apparatus (not shown). Luer lock 34 provides a seal between the monomer dispensing device 1 and the mixing apparatus preventing toxic vapors from escaping into the atmosphere at this connection. Monomer dispensing device 1, therefore, creates a closed system whereby the monomer can safely be added to the bone cement.

Monomer dispensing device 1 can be made from a variety of materials. Components from device 1 can be made from most types of plastic, glass, metal, or combinations thereof. One preferred embodiment of device 1 is that it be disposable. Plastic materials like polypropylene or polyethylene are preferable so that after device 1 has deposited the monomer it can be discarded. Because no components of device 1 are disassembled, no residual monomer or vapors will escape. It may be preferable, however, to use a plastic material that will not degrade if it comes into contact with a ketone. Plastics like polycarbonate will work, even though it will eventually degrade when in contact with the monomer, as long as the monomer is dispensed and the device 1 is discarded immediately after severing the ampule 4.

Figure 3:
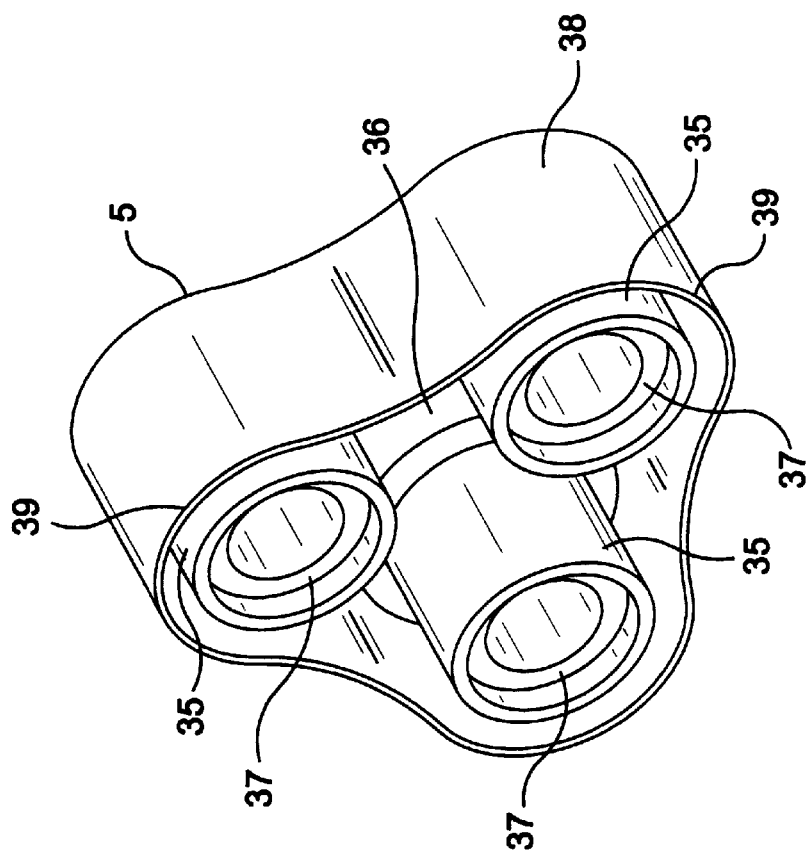
FIG. 3 is a perspective view of a portion of FIG. 2, showing the end cap having a base, post apertures, post stops, an edging attached to the base and a rim attached to the edging.

A perspective view of illustrative end cap 5 is shown in FIG. 3. End cap 5 comprises a post aperture 35. Monomer delivery device 1 can comprise a plurality of ampule chambers 3 (see FIG. 6). End cap 5 will, therefore, be configured with the same number of post apertures 35 as number of aperture chambers 3 provided in body 2 with the shape and size of end cap 5 to conform accordingly. In one illustrative embodiment, post aperture 35 is a cylindrical structure extending from base 36. On the end of post aperture 35 opposite from base 36, a post stop 37 is circumferentially formed around the inner circumference of post aperture 35. Post stop 37 limits the size of the encapsulated portion of ampule chamber 3 by limiting range of movement of post 6. Post stop 37 also prevents post 6 from being pushed out of ampule chamber 3 thereby breaking the seal between post 6 and inner wall 26 (see FIG. 1). In addition, an object can extended through end cap 5 and post aperture 35 to push against post 6 thereby securing ampule 4 as previously discussed.

End cap 5 also comprises an edging 38 extending from base 36 and surrounding post aperture 35 contouring the outer perimeter of load end 9 of body 2. (See FIG. 3.) Opposite base 36, on edging 38 is a rim 39. Rim 39 attaches to load end 9 after ampule 4 and posts 6 have been inserted into ampule chambers 3. In one embodiment end cap 5 attaches to load end 9 of body 2 by press fitting rim 39 into body 2. In an alternative embodiment, rim 39 can attach to body 2, after ampules 4 have been inserted into ampule chamber 3, using an adhesive, ultrasonic welding or snap-fit.

Figure 5:
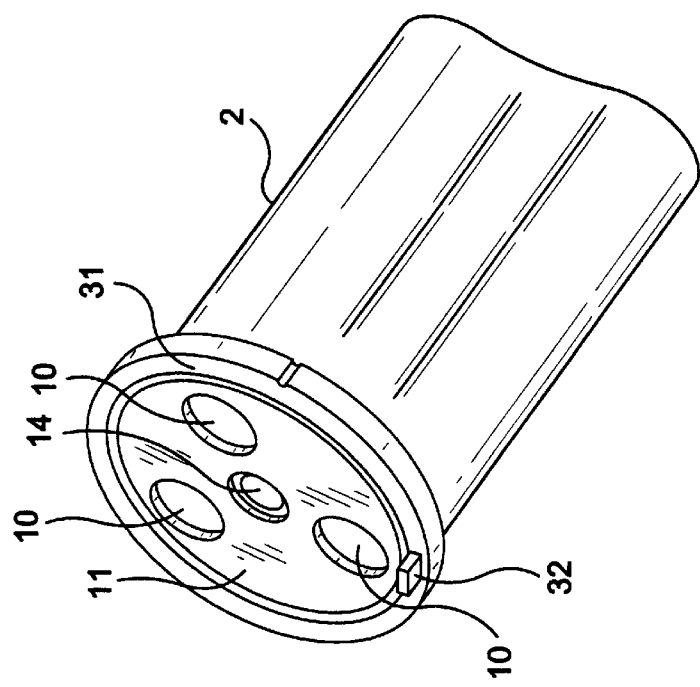
FIG. 5 is a front perspective view of a portion of the monomer delivery device from FIG. 2, showing the body having a plurality of apertures, a collar aperture and a flange.
Figure 7:
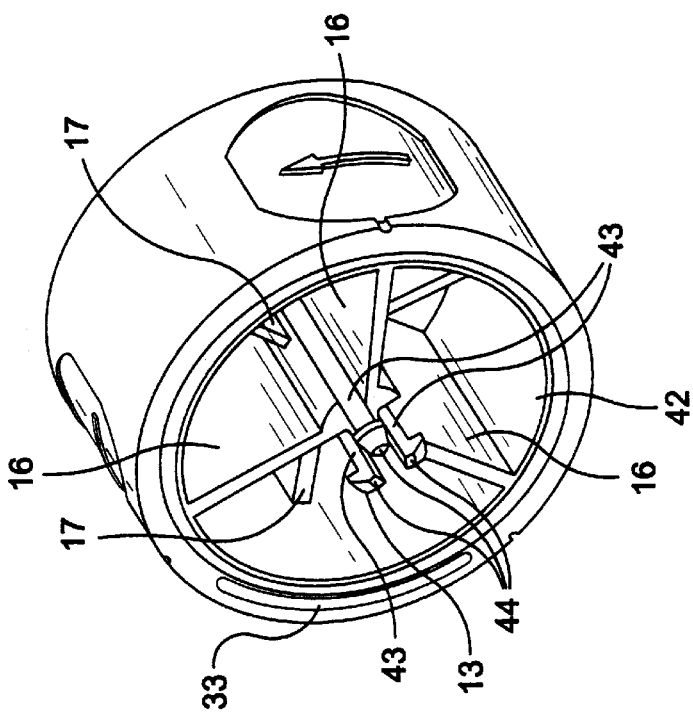
FIG. 7 is a front perspective view of a portion of the monomer delivery device from FIG. 2, showing the rotating collar having a plurality of half blades and full blades.

A front perspective view of body 2 is shown in FIG. 5. Cap end 11 comprises a plurality of apertures 10 disposed therethrough. Each one of a plurality of apertures 10 are axially aligned along the longitudinal axis of each of a plurality of ampule chambers 3, and in tandem arrangement with same. Each aperture 10 is sized to receive extending ampule cap 8 but prevent ampule 4 itself from extending therethrough. As also shown in FIG. 7, one preferred embodiment comprises collar aperture 14 disposed through generally the center of cap end 11.

Figure 6:
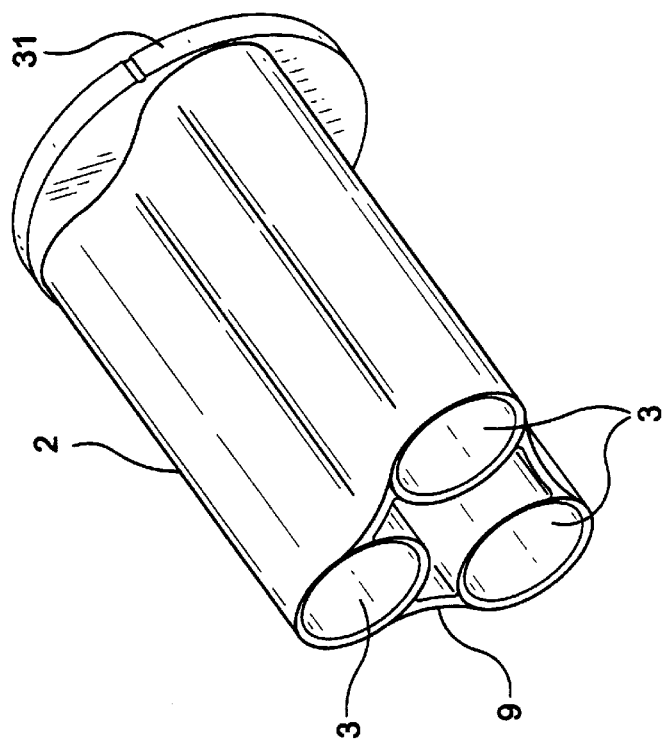
FIG. 6 is a rear perspective view of a portion of the monomer delivery device from FIG. 2, showing the body having a load end and a cap end, a plurality of ampule chambers and the flange.

A rear perspective view of body 2 is shown in FIG. 6, having a plurality of ampule chambers 3 accessible at load end 9. Ampules 4 are loaded from load end 9 and positioned through chamber 3 until ampule cap 8 is extended through aperture 10 as previously discussed. After ampule 4 is loaded into ampule chamber 3, post 6 with medium o-ring 24 attached, is placed inside ampule chamber 3 to seal load end 9. Finally, end cap 5 is attached to load end 9 of body 2 in a manner previously discussed. (See FIG. 1).

Figure 9:
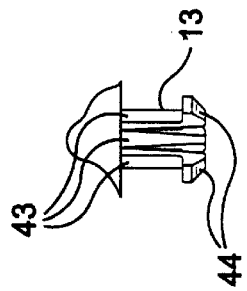
FIG. 9 is a side elevation view of a portion of the monomer delivery device from FIG. 1, showing the collar lock.
Figure 14:
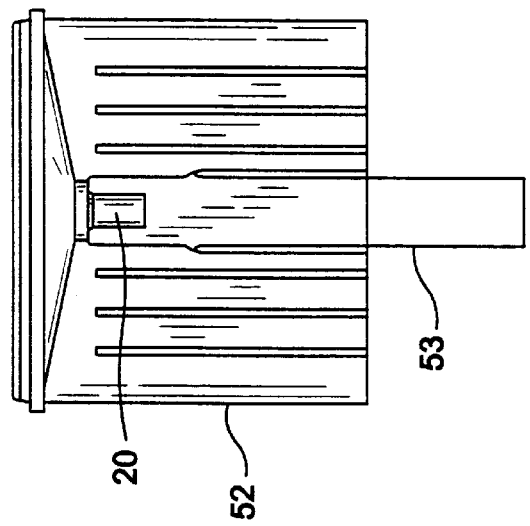
FIG. 14 is a side view of the funnel and guide from FIG. 13 showing an extended spout attached to the funnel.

A side elevation view of collar lock 13 is shown in FIG. 9. Collar lock 13 comprises a plurality of depending prongs 43, with protruding tongues 44 extending from the end thereof. Small o-ring 27 is placed around the plurality of prongs 43 (see FIG. 1). Collar lock 13 then extends through collar lock aperture 14 on body 2(see FIGS. 1 and 2). Together, prongs 43 create substantially the same diameter as collar aperture 14. However, prongs 43 are sufficiently bendable, yet sufficiently elastic at the same time, and have tongues 44 so configured that collar lock 13 can compress to fit through collar lock aperture 14 and return to its original shape. Tongues 44 then extend past the thickness of collar aperture 14 thereby rotatably securing collar 12 to body 2.

It is understood that collar lock 13 can be configured in any manner that rotatably attaches collar 12 to body 2. For example, rather than using three small bendable prongs, two larger bendable prongs might be used, or simply one compressible prong or equivalent structure. Or a still further example, collar 12 may movably snap fit about cap end 11 of body 2 (not shown). With large o-ring 29 fitted into groove 30, and small o-ring 27 fitted into groove 28, a seal is created between collar 12 and body 2 as previously discussed. (See FIG. 2.)

Figure 10:
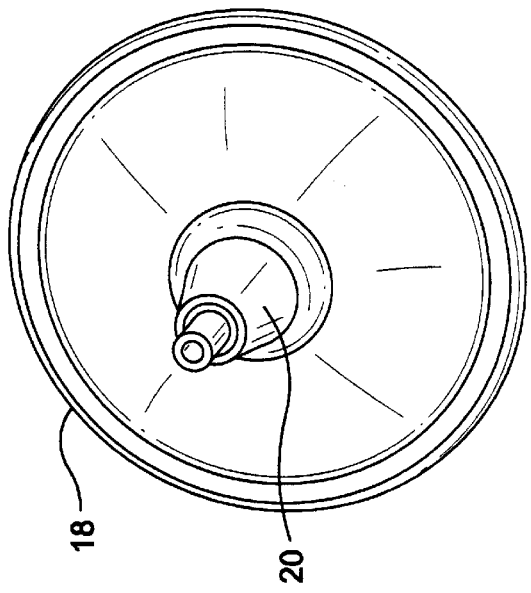
FIG. 10 is a front perspective view of a portion of the monomer delivery device from FIG. 1, showing the funnel.

A front perspective view of funnel 18 is shown in FIG. 10. Funnel 18 has a conically shaped body concluding at spout 20. The conical shape of funnel 18 at spout 20, in this embodiment, is steeper than at the outer edge of funnel 18. It is understood that funnel 18 can have any conical shape, or even none at all, or have a variable conical shape as it concludes to spout 20. In addition, another embodiment of the present invention can have a spout 20 located anywhere on funnel 18. Also, as illustratively shown in FIG. 11, a step structure 45 that attaches funnel 18 to collar 12. Around the circumference of top surface 41 of collar 12 is a ridge 46 as shown in FIG. 7. Ridge 46 corresponds to stepped structure 45 creating a seal between collar 12 and funnel 18 when ultrasonic welded together. It is understood that collar 12 and funnel 18 can be attached by various other means including adhesive, press fit or snap-lock.

Figure 11:
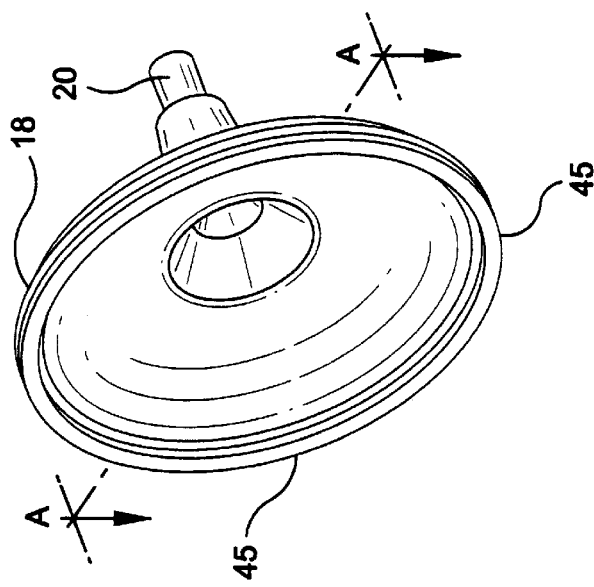
FIG. 11 is a rear perspective view of the funnel from FIG. 10, showing the spout and the step structure.
Figure 12:
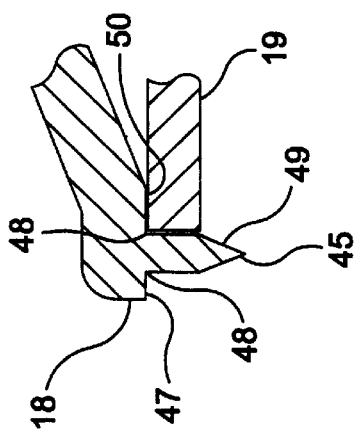
FIG. 12 is a fragmentary cross sectional view of the funnel from FIG. 11, showing the stepped structure taken along cross section A—A in FIG. 11.

A cross sectional view of funnel 18 along line A—A in FIG. 11, is shown in FIG. 12, illustrating the detail of step structure 45. Step structure 45 comprises a narrowly portioned ledge 47 along the outer perimeter of funnel 18. Step 48 forms a thicker portioned tongue 49 with another step 47 forming a narrowly portioned screen ledge 50. When funnel 18 is attached to collar 12, ledge 47 is placed on ridge 46 from collar 12 as previously discussed. Tongue 19 is fitted into tongue groove 51 in collar 12, with screen 19 placed between surface end 41 of collar 12 and screen ridge 50. It is understood that screen 19 is not limited to a particular material or to the traditional weave netting configuration. Screen 19 merely prevents any material from traveling past collar 12. For example, screen 19 can be a porous material filter, or a randomly directional strand mesh.

Figure 13:
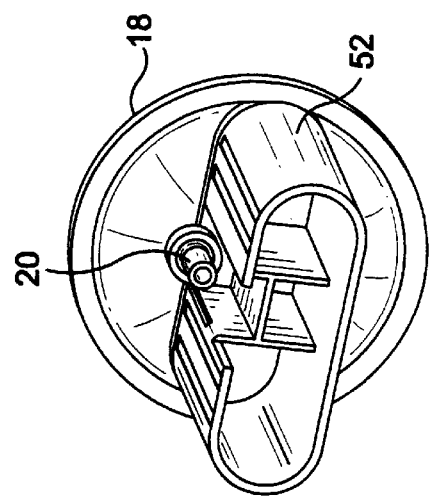
FIG. 13 is a perspective view of the funnel from FIG. 11, showing a guide located near the spout.

Funnel 18 is shown in FIG. 13 having guide 52 located near the spout 20. Guide 52 is used for certain types of cement mixing devices (not shown). An extended spout is shown in a side view of funnel 18 and guide 52 in FIG. 14. Extended spout 53, used in cooperation with guide 52 is specifically suited for dispensing monomer in longitudinal-type cement mixers (not shown). In another embodiment (not shown), extended spout 53 may be fitted to valve 21 thereby extending the valve so it may fit either into a differently configured bone cement mixing bowl, into luer lock 34 that mates with the bone cement mixing bowl.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as set forth in the following claims.

What is claimed is:

1. A device for breaking an ampule of monomer in a sealed structure and dispensing monomer, the device comprising:
   a body providing a chamber for receiving an ampule of monomer, and a spout for dispensing monomer from the ampule; and a collar rotatably attached to the body having a blade attached within the collar and configured to sever the ampule, wherein rotation of the collar relative to the body causes the blade to contact and sever the ampule.

2. The monomer dispensing device of claim 1, wherein the body provides a plurality of chambers sized to receive a plurality of ampules of monomer.

3. The monomer dispensing device of claim 1, further comprising a valve attached to the spout, the valve having a valve closure that allows monomer to flow out of the valve when the closure is disengaged, and prevents monomer from flowing out of the valve when the closure is engaged.

4. The monomer dispensing device of claim 1, further comprising a funnel attached to the collar and wherein the spout attaches to the funnel which attaches to the collar.

5. The monomer dispensing device of claim 4, further comprising a screen fitted between the collar and the funnel, and having a screen mesh sized to allow monomer to pass from the collar to the funnel yet to prevent particles of the severed ampule from passing through the mesh.

6. A device for breaking an ampule monomer in a sealed structure and dispensing monomer, the device comprising:
a body providing a chamber for receiving an ampule of monomer, and a spout for dispensing monomer from the ampule; and
a collar attached to the body having a blade attached within the collar and configured to sever the ampule,
wherein the body provides a plurality of chambers sized to receive a plurality of ampules of monomer, and
wherein the collar is rotatable relative to the body and comprises a plurality of blades.

7. The monomer dispensing device of claim 6, wherein the plurality of blades comprises an alternating half blade and full blade.

8. A device for breaking an ampule of monomer in a sealed structure and dispensing monomer, the device comprising:
a body providing a chamber for receiving an ampule of monomer, and a spout for dispensing monomer from the ampule;
a collar attached to the body having a blade attached within the collar and configured to sever the ampule; and
a flange fitted on the body between the body and the collar creating a rotary seal between the body and the collar.

9. A device for dispensing monomer from an ampule having an ampule cap, the device comprising:
a cylindrical body having a longitudinal axis and a longitudinal chamber defining a load end and a cap end and disposed about the axis, the chamber for receiving an ampule of monomer from the load end and where an aperture is disposed through the cap end through which the ampule cap extends;
a collar mounted on the cap end to rotate about the axis, the collar having portions thereof engageable with the ampule cap when the collar is rotated, and the collar being pivotally attached to the cap end of the body and positioned to receive the ampule cap extended through the aperture, and further the collar has a blade configured to sever the ampule cap when the collar is rotated;
a post positioned inside the chamber abutting the ampule thereby securing the ampule within the chamber;
an end cap attached to the load end of the body and having a post stop limiting movement of the post;
a funnel fitted on the collar opposite the body such that as the blade from the collar severs the ampule cap, monomer is released from the ampule and collects in the funnel;

a screen, placed between the collar and the funnel preventing particles from the severed ampule cap from traveling past the collar; and
a spout attached to the funnel that expels collected monomer.

10. The monomer dispensing device of claim 9, wherein the body provides a plurality of chambers sized to receive a plurality of ampules of monomer.

11. The monomer dispensing device of claim 10, wherein the collar comprises a plurality of blades.

12. The monomer dispensing device of claim 11, wherein the plurality of blades comprises an alternating half blade and full blade.

13. The monomer dispensing device of claim 9, further comprising a valve attached to the spout, the valve having a valve closure that allows monomer to flow out of the valve when the closure is disengaged, and prevents the monomer from flowing out of the valve hole when the closure is engaged.

14. The monomer dispensing device of claim 13, further comprising a luer lock configured to attach to the valve to mate with a mixing apparatus providing a seal between the monomer dispenser and the mixing apparatus, and preventing toxic vapors from escaping the dispensing device.

15. A monomer dispensing device, comprising:
a body defining a chamber for receiving at least a part of an ampule of monomer; and
a collar movably attached to the body and defining an interior collar space, the collar having at least one blade located within the interior collar space,
wherein (i) the ampule of monomer has an end cap which extends into the interior collar space when the ampule of monomer is located in the chamber of the body, and (ii) movement of the collar relative to the body causes the at least one blade to contact the end cap within the interior collar space thereby severing the ampule.

16. The monomer dispensing device of claim 15, further comprising a funnel attached to the collar and operable to collect monomer released from the ampule after the ampule is severed.

17. The monomer dispensing device of claim 16, further comprising a screen positioned between the collar and the funnel and operable to prevent ampule particles from advancing from the collar to the funnel.

18. The monomer dispensing device of claim 17, wherein said funnel includes a spout through which monomer may advance.

19. A monomer dispensing device, comprising:
a body defining a chamber for receiving at least a part of an ampule of monomer; and
a collar rotatably attached to the body and defining an interior collar space, the collar having at least one blade located within the interior collar space, wherein (i) the ampule of monomer has an end cap which extends into the interior collar space when the ampule of monomer is located in the chamber of the body, and (ii) rotation of the collar relative to the body causes the at least one blade to contact the end cap within the interior collar space thereby severing the ampule;
a funnel attached to the collar and operable to collect monomer released from the ampule after the ampule is severed; and
a screen positioned between the collar and the funnel and operable to prevent ampule particles from advancing from the collar to the funnel.

20. The monomer dispensing device of claim 19, wherein said funnel includes a spout through which monomer may advance.

* * * * *